United States Patent

Heneveld et al.

[11] Patent Number: 6,080,113
[45] Date of Patent: Jun. 27, 2000

[54] INCISIONAL BREAST BIOPSY DEVICE

[75] Inventors: Scott Heneveld, Hickory Corners; Mark Zyzelewski, Plainwell; Warren D. Lun, Battle Creek; Mark A. Penrod, Delton, all of Mich.

[73] Assignee: Imagyn Medical Technologies California, Inc., Newport Beach, Calif.

[21] Appl. No.: 09/151,439

[22] Filed: Sep. 11, 1998

[51] Int. Cl.[7] .................................................. A61B 10/00
[52] U.S. Cl. ..................... 600/564; 600/562; 600/568; 606/170
[58] Field of Search .................................. 600/562, 564, 600/566, 567, 568; 606/130, 167, 170, 180

[56] References Cited

U.S. PATENT DOCUMENTS

| | | | |
|---|---|---|---|
| 5,111,828 | 5/1992 | Kornberg, et al. | 600/567 |
| 5,133,360 | 7/1992 | Spears | 600/567 |
| 5,197,484 | 3/1993 | Kornberg et al. | 600/567 |
| 5,353,804 | 10/1994 | Kornberg et al. | 600/567 |
| 5,573,008 | 11/1996 | Robinson et al. | 600/567 |
| 5,645,556 | 7/1997 | Yoon | 606/185 |
| 5,687,739 | 11/1997 | McPherson et al. | 600/567 |
| 5,782,775 | 7/1998 | Milliman et al. | 600/567 |
| 5,795,308 | 8/1998 | Russin | 600/567 |
| 5,807,276 | 9/1998 | Russin | 600/567 |
| 5,810,806 | 9/1998 | Ritchart et al. | 606/45 |
| 5,817,034 | 10/1998 | Milliman et al. | 600/564 |
| 5,830,219 | 11/1998 | Bird et al. | 600/568 |

FOREIGN PATENT DOCUMENTS

| | | |
|---|---|---|
| 0 761 170 | 3/1997 | European Pat. Off. . |
| 534 505 | 3/1973 | Switzerland . |

*Primary Examiner*—Cary O'Connor
*Assistant Examiner*—Charles Marmor
*Attorney, Agent, or Firm*—Howard & Howard

[57] ABSTRACT

A breast biopsy device is provided which includes a localization needle having a guide wire preloaded into the biopsy device. The device includes a stylet having a blade for transecting and separating healthy tissue on route to the biopsy site. The use of the stylet blade reduces the trauma to healthy breast tissue. The device further includes a cannula blade and a garrote for forming a cut transverse to the core cut by the cannula blade. A lockout feature prevents the garrote from deploying until after a cutting plane of the garrote has been advanced beyond the end of the guide wire.

18 Claims, 10 Drawing Sheets

INCISIONAL BREAST BIOPSY DEVICE

BACKGROUND OF THE INVENTION

This invention relates generally to surgical instruments and, more particularly, to a device for percutaneous incisional breast biopsy.

The early diagnosis of breast cancer through the use of mammography is very important for reducing the morbidity associated with breast cancer. Early diagnosis enables a physician to treat the breast cancer at a more manageable stage of development.

Mammography is capable of detecting very small abnormalities in breast tissue. However, mammography usually cannot differentiate between malignant and benign lesions in the breast. Definitive determination of the status of a lesion often requires a histological examination of the suspect tissue.

One method for obtaining a tissue sample for histological examination is through a biopsy of part or all of the suspect tissue. There are a number of devices and methods for performing a biopsy of the breast. Generally, the procedure requires first placing a localization needle within or near the lesion. A guide wire contained within the localization needle is then deployed. The guide wire usually includes hooks that anchor one end of the guide wire in breast tissue near the lesion. Then a biopsy device that includes a cannula and a stylet that is located within the cannula is inserted over the localization needle and guide wire. The device is inserted through a small incision in the breast tissue near the entry point of the localization needle. The stylet bluntly separates breast tissue as the device is inserted down the guide wire toward the lesion. Advancement of the device is stopped once the tip of the stylet is within or near the lesion. Then, the cannula, which has a cutting surface at its leading edge, is advanced over the stylet and into the tissue thereby cutting a core of tissue. The cutting surface is advanced to a point beyond the end of the guide wire. Then, a second cutting surface, typically a wire garrote, is activated to perform a cut transverse to the direction the cannula and beyond the end of the guide wire. This second cut releases a plug from the lesion. Then the needle, guide wire, and device are retracted from the breast with the plug. The plug is then histologically examined to determine whether the suspect tissue is malignant or benign.

The current devices have a number of disadvantages including: the device, localization needle, and guide wire are not manufactured as a single unit; and the devices generally do not have a means for insuring that the garrote wire is located past the end of the guide wire prior to deployment of the garrote. In order to determine whether the garrote is located past the end of the guidewire, a radiographic check is required. Further, the blunt stylet requires substantial force to insert and may cause trauma to the healthy tissue as it passes to the biopsy site.

Therefore, it is desirable to provide a biopsy device manufactured as a unit with a localization needle and a guide wire. Additionally, it is desirable to provide a biopsy device having features to insure that the garrote wire is not deployed until it is past the end of the guide wire. It is also desirable to provide a stylet with cutting members to transect and separate breast tissue and minimize the damage to healthy tissue.

SUMMARY OF THE INVENTION

The present invention overcomes the problems with previous biopsy devices by providing a biopsy device which is manufactured with an integral localization needle and guide wire. In addition, the invention includes means for insuring that the garrote wire is not deployed until the garrote wire is beyond the end of the guide wire. Further, the stylet is provided a blade which transects tissue as the device is inserted to the biopsy site.

According to one aspect of the present invention, the device includes a cannula having a shaft with a cutting surface on one end of the shaft and the other end of the shaft in engagement with a drive assembly. Adjacent to the cutting surface of the cannula is a second cutting mechanism for making a cut transverse to the cut made by the cannula cutting surface. Located within the cannula shaft is a stylet. The stylet has a tip portion with a blade for transecting and separating tissue and a central chamber for permitting a localization needle to pass through the length of the stylet. The localization needle has an interior chamber permitting passage of a guide wire through the length of the localization needle. The device also includes a lock feature for preventing deployment of the second cutting mechanism until it is past the end of the guide wire.

According to a further aspect of the present invention, a method of removing suspect breast tissue with a breast biopsy device includes the steps of inserting a localization needle into tissue, advancing a hooked guide wire out of a distal end of the localization needle to anchor the biopsy device in the tissue in or near a lesion, advancing a stylet and cannula manually over the localization needle until the stylet is adjacent the lesion, advancing the cannula blade to cut a core of tissue, unlocking a trigger of a garrote when a cutting plane of the garrote has been advanced past a distal end of the guide wire, and moving the trigger to activate the garrote and make a cut transverse to a direction of advancement of the cannula.

DETAILED DESCRIPTION OF THE PREFERRED EMBODIMENT

Figure 1:
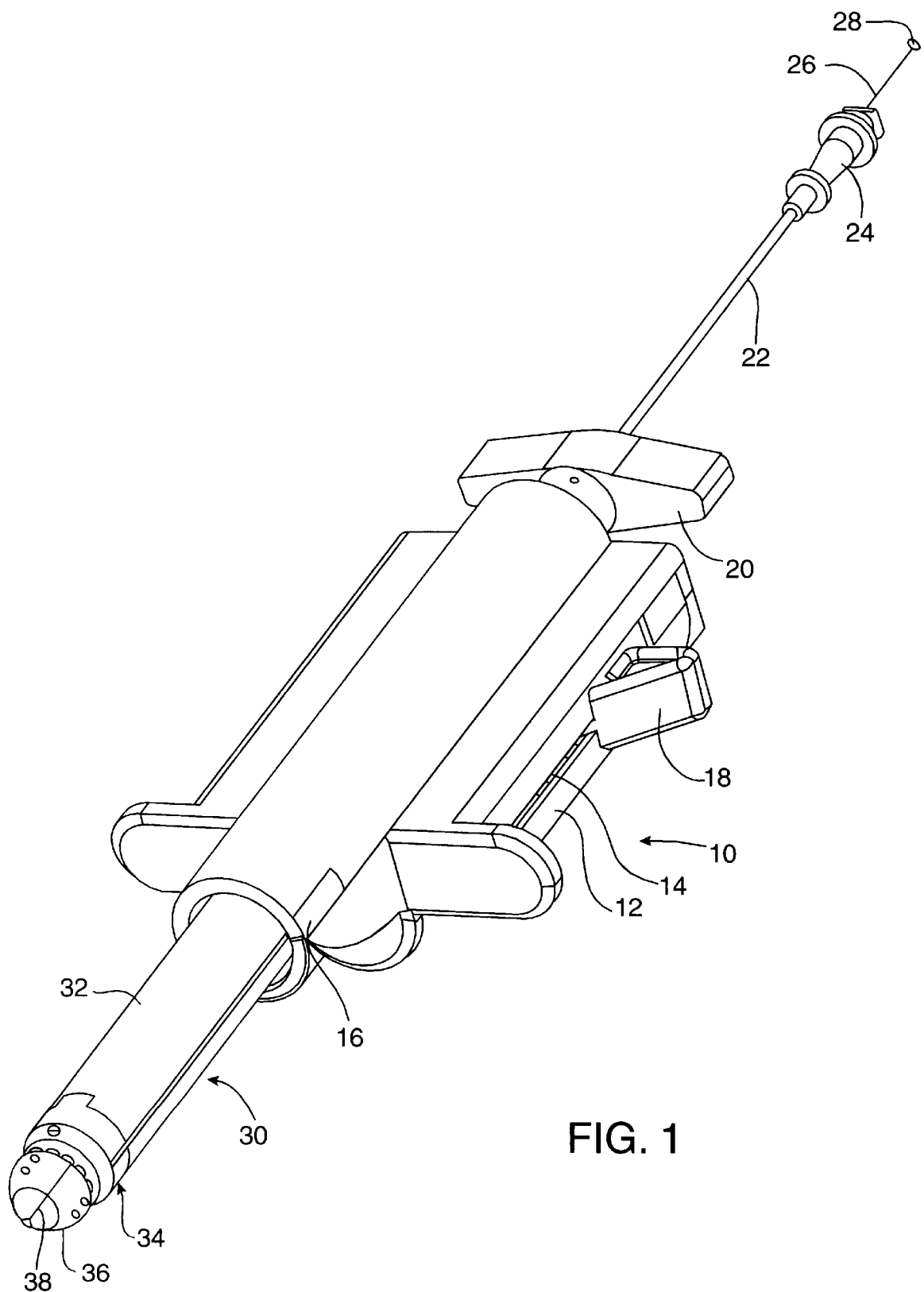
FIG. 1 is a perspective view of a biopsy device designed according to the invention.

Referring to the figures wherein like numerals indicate like or corresponding parts throughout the several views, in FIG. 1 a biopsy device is shown generally at 10. The device 10 includes an exterior housing 12 having a trigger slot 14 and a window 16. A trigger 18 extends through the trigger slot 14. A stylet retractor handle 20 is mounted adjacent a rear end of the exterior housing 12. A localization needle 22 is received within the retractor handle 20. A hub 24 is mounted on a distal end of the localization needle 22. A guide wire 26 is slidably received within the localization needle 22. A stop 28 is mounted on one end of the guide wire 26. A cannula 30 extends from a front portion of the exterior housing 12. The cannula 30 comprises a shaft 32 and a nosepiece 34. A stylet 36 having a diameter less than the diameter of the shaft 32 extends beyond the nosepiece 34 of the cannula 30. A blade 38 is mounted within the stylet 36 for transecting and separating tissue as the device is inserted to the biopsy site.

In use, the biopsy device 10 is inserted by inserting the localization needle 22 into the tissue and deploying the guidewire 26 within the localization needle to anchor the device in the breast tissue. The cannula 30 and stylet 36 are then advanced over the localization needle with the stylet transecting and separating the healthy breast tissue with minimal trauma to the healthy tissue as the cannula is inserted toward the lesion. The cannula 30 is then advanced to cut a core of tissue. A garrote having a looped section of wire is provided within a recess in the forward end of the cannula. The trigger 18 is used to activate the garrote and cut the tissue plug in a direction transverse to the direction in which the cannula 30 was advanced. The trigger 18 is provided with a locking mechanism, as will be described below, for preventing deployment of the garrote prior to movement of a cutting plane of the garrote past an end of the guidewire 26.

Figure 2:
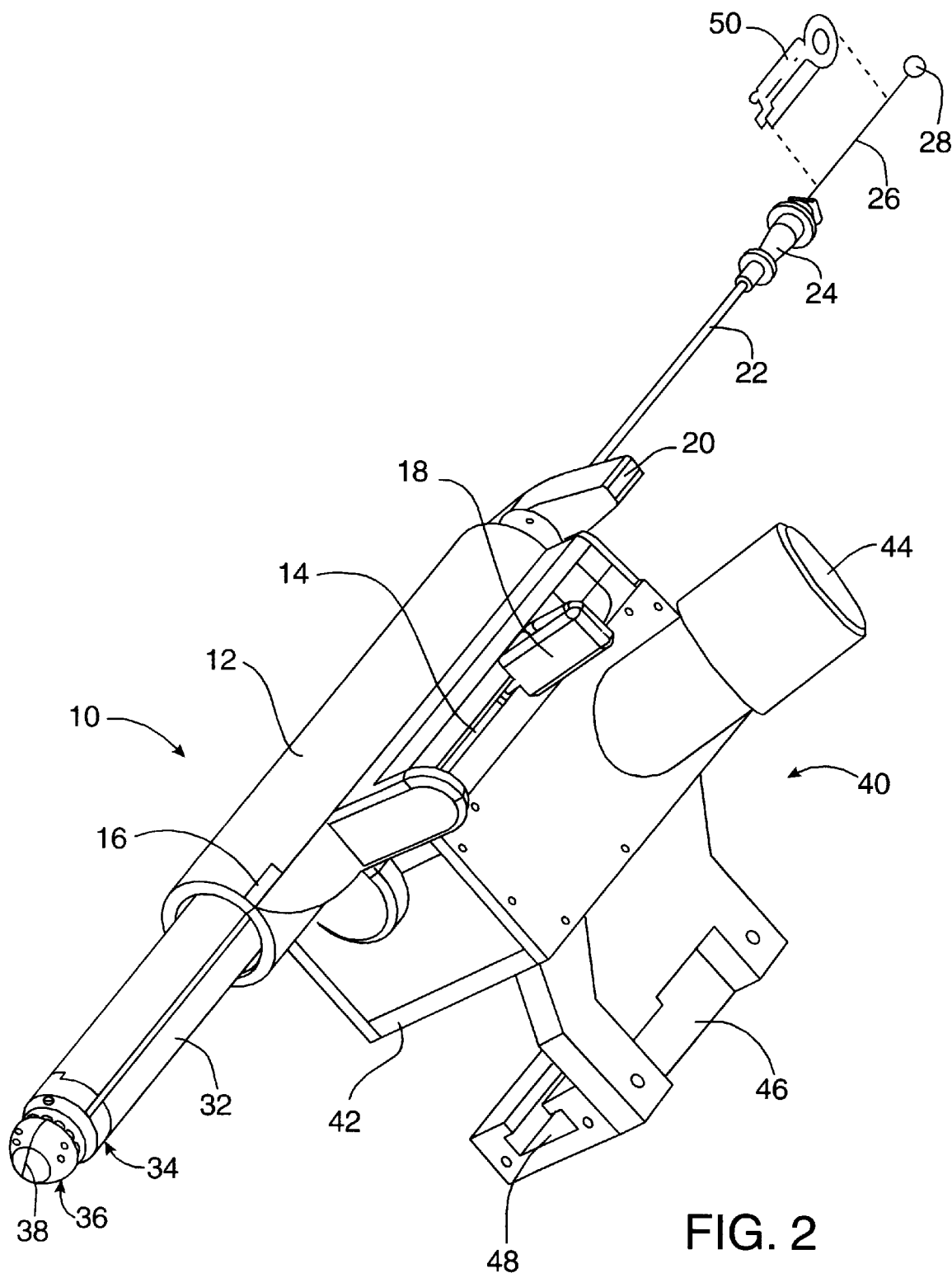
FIG. 2 is a perspective view of a biopsy device designed according to the invention mounted on an instrument holder.

In FIG. 2, the device 10 is shown mounted on an instrument holder 40. The instrument holder 40 includes a housing 42 and an adjustment knob 44 mounted within the housing 42. A bracket 46 connects the housing 42 to a track 48. The track 48 can be fixed at a point along a rail (not shown) by a friction cam brake (not shown). A safety wrapper 50 is shown adjacent an end of the guide wire 26. The safety wrapper 50 is removable prior to deployment of the guide wire 26 and serves to prevent premature deployment of the guide wire 26. The function of the safety wrapper 50 may also be incorporated in the packaging for the device to prevent premature deployment during transport.

Figure 3:
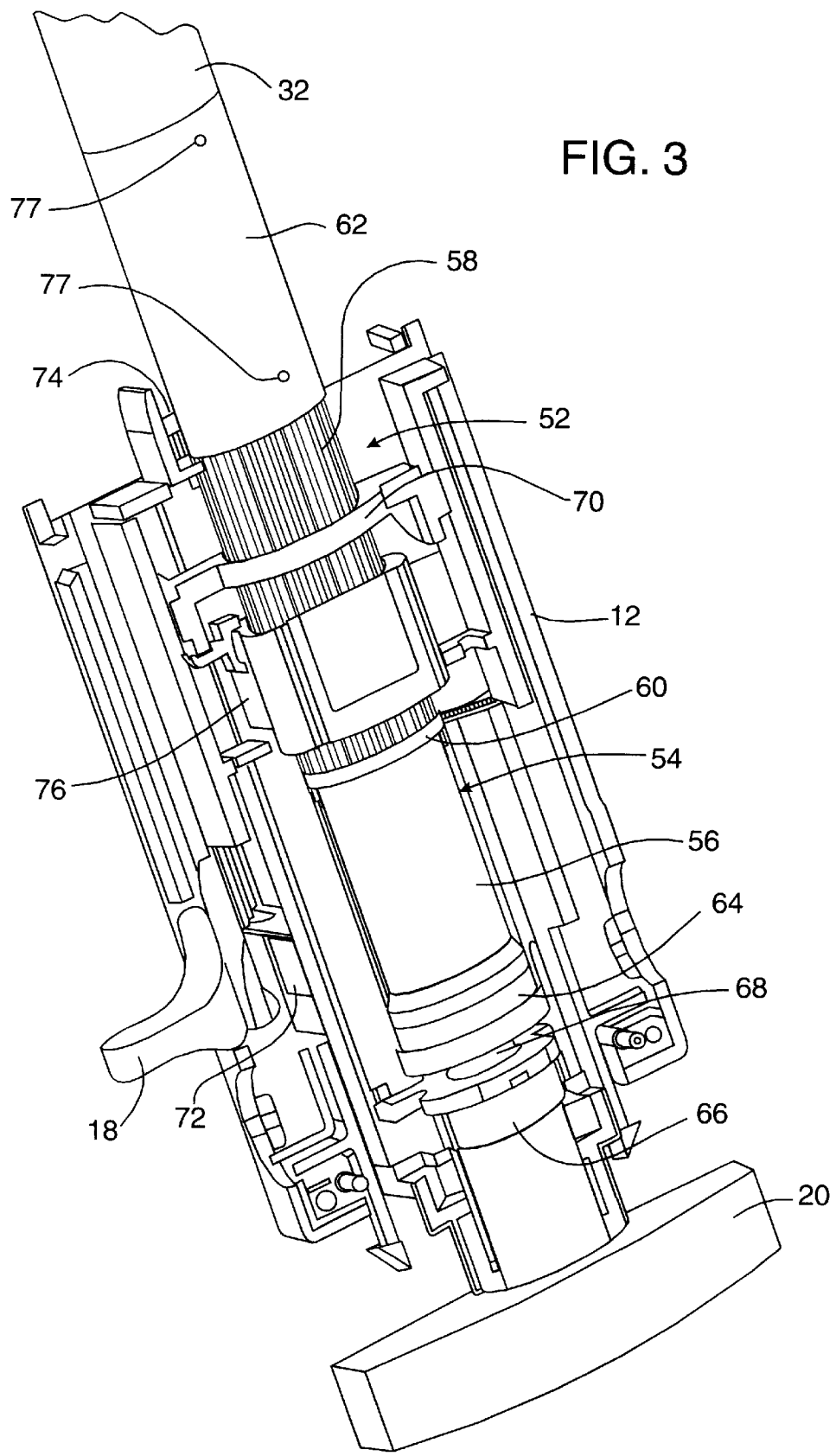
FIG. 3 is a top perspective view of a biopsy device with a portion of the exterior housing removed.

In FIG. 3, a top view of the device 10 with a portion of the exterior housing 12 removed is shown. A drive assembly 52 is mounted within the exterior housing 12. The drive assembly 52 includes a spline 54 having a cylindrical member 56 and a gear member 58 separated by a shoulder 60. A connector 62 engages the spline 54 with the shaft 32 of the cannula 30. A sleeve 64 is mounted on the cylindrical member 56. A screw base 66 is mounted within the exterior housing 12. A lead screw 68 is mounted to the screw base 66 and extends into the spline 54. A finger sleeve 70 is mounted within the exterior housing 12 and encircles the gear member 58. A finger 72 is attached to the finger sleeve 70. A gear drive 74 is mounted below the geared member 58 and engages the geared member 58. A collar 76 encircles the spline 54 and is mounted within the exterior housing 12. The connector 62 includes a series of fasteners 77.

Figure 4:
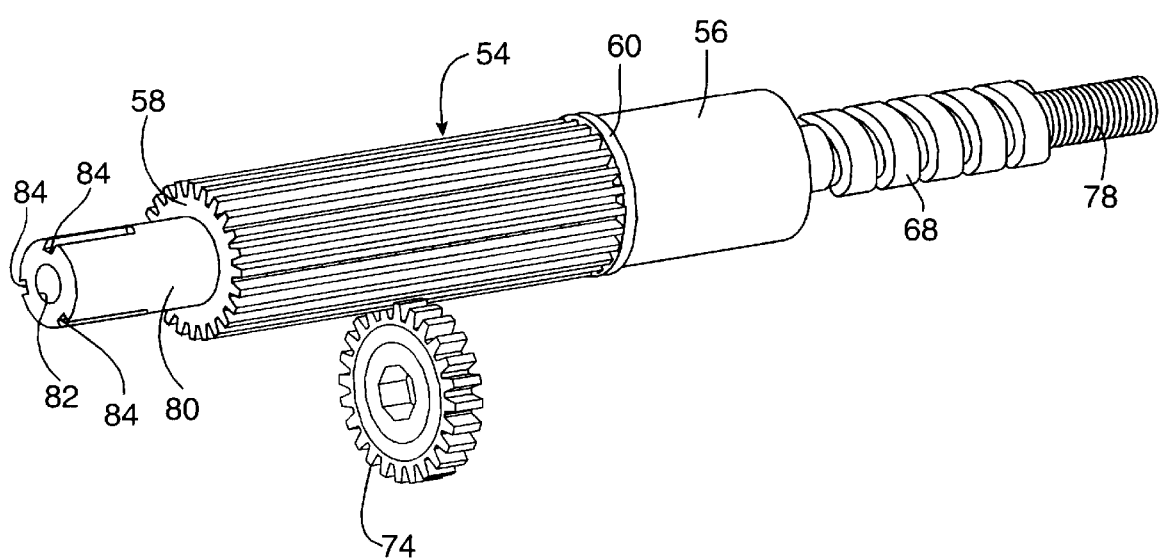
FIG. 4 is a perspective view of the drive assembly of a biopsy device designed according to the invention.

In FIG. 4, an enlarged view of the drive assembly 52 is shown. A threaded member 78 extends from a rear portion of the lead screw 68. The threaded member 78 threads into the screw base 66 (not shown). A connector shaft 80 extends from the front of the geared member 58. A central passage 82 extends through the connector shaft 80, spline 54, lead screw 68, and the threaded member 78. The central passage 82 accommodates the localization needle 22 (not shown). The connector shaft 80 includes several slots 84 for receiving the fasteners 77 of the connector 62.

Figure 5A:
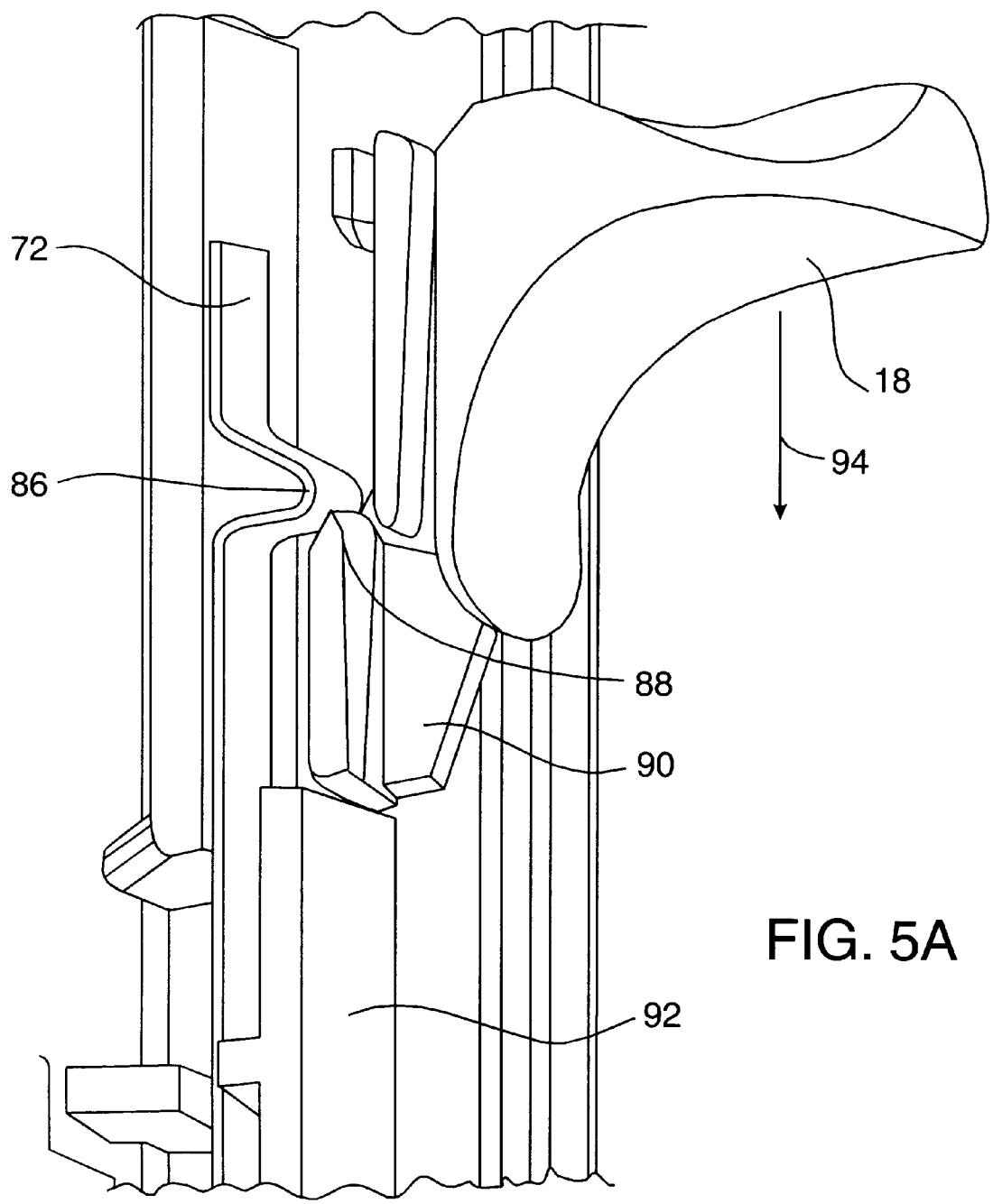
FIG. 5A is an enlarged perspective view of a portion of the trigger of the biopsy device in the locked position.
Figure 5B:
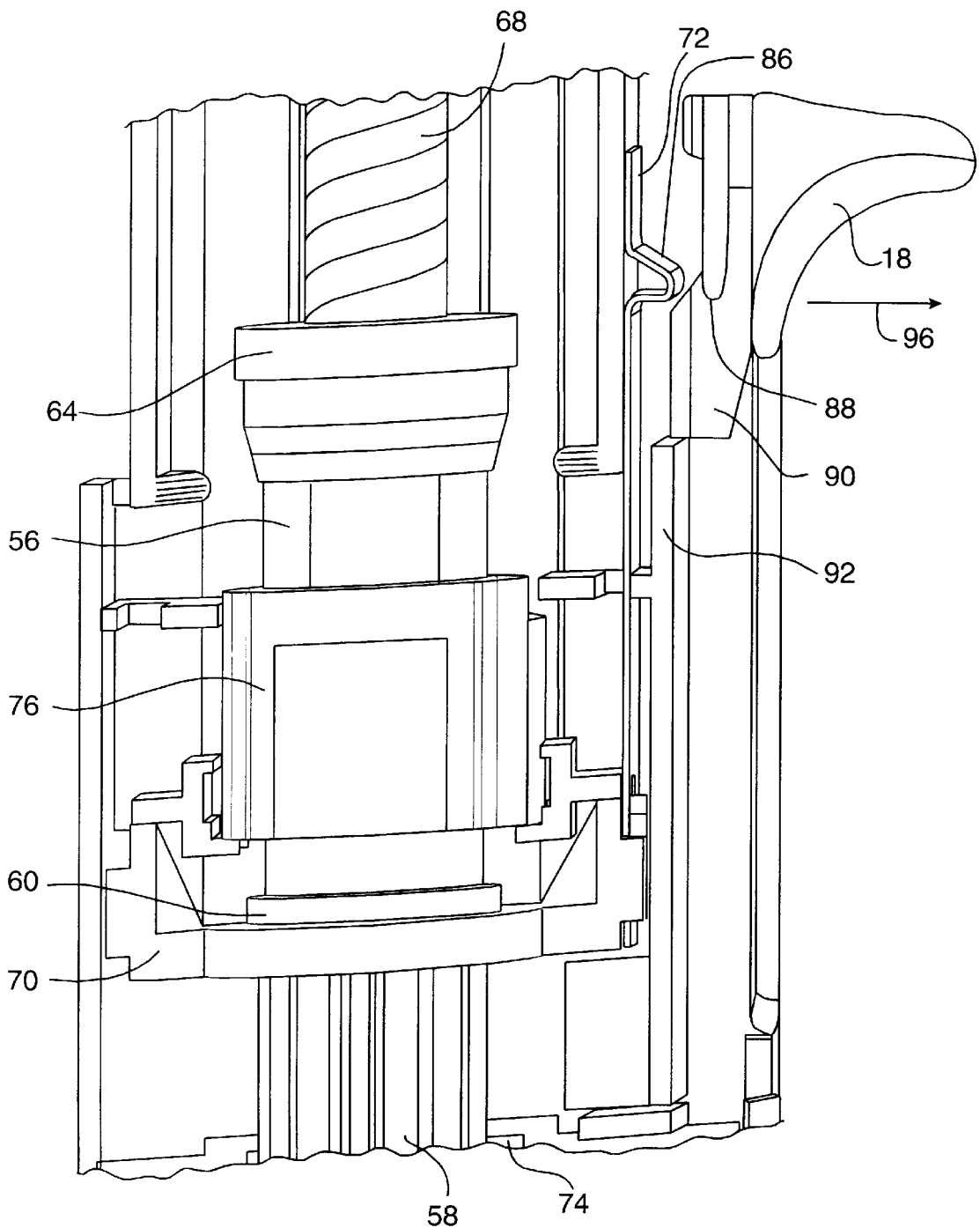
FIG. 5B is a perspective view of a portion of the biopsy device with the trigger in the partially unlocked position.
Figure 5C:
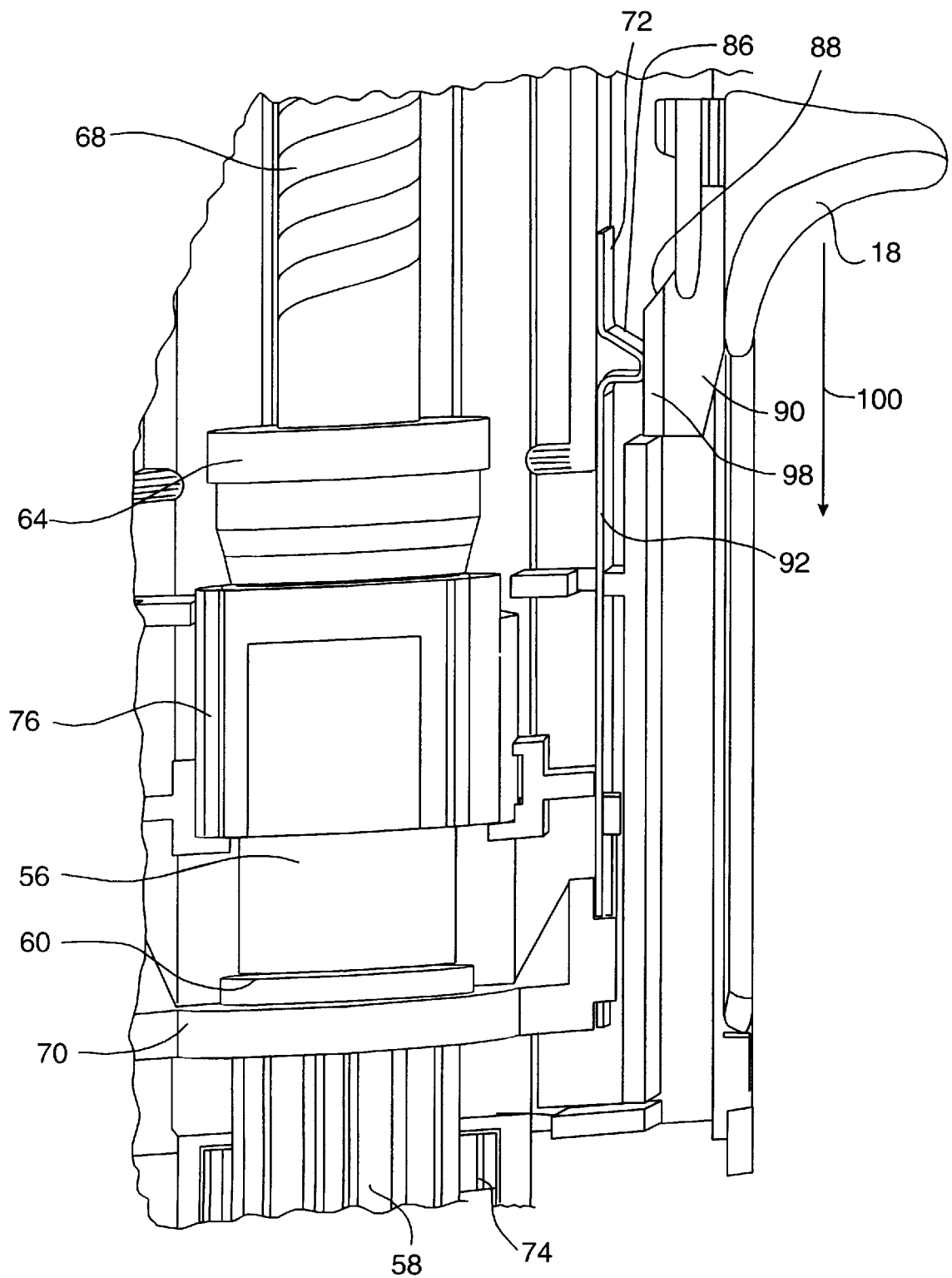
FIG. 5C is a perspective view of a portion of the biopsy device with the trigger in the fully unlocked position.

In FIGS. 5A–5C, the trigger 18 is shown in the three stages of fully locked, partially unlocked, and fully unlocked, respectively. In FIG. 5A, the trigger 18 is shown in the fully locked position. A V-shaped bend 86 in the finger 72 is positioned adjacent a ramped portion 88 of a trigger bracket 90. A stop 92 formed in the exterior housing 12 prevents the trigger 18 from moving in the direction of arrow 94 toward the cannula 30 (not shown).

In FIG. 5B, the trigger 18 is shown in the partially unlocked position. Rotation of the adjustment knob 44 (not shown) rotates the drive gear 74 which in turn rotates the gear member 58. Rotation of the gear member 58 causes movement of the spline 54 along the length of the lead screw 68. When the shoulder 60 advances sufficiently to contact the finger sleeve 70, additional forward movement of the spline 54 pulls the finger sleeve 70 and the attached finger 52 forward. Advancement of the finger 72 causes the V-shaped bend 86 to ride up the ramped portion 88 of the trigger bracket 90. The movement of the V-shaped bend 86 pushes the trigger 18 outwardly in the direction of arrow 96.

In FIG. 5C, the trigger 18 is shown in the fully unlocked position. As further rotation of the gear drive 74 causes further advancement of the spline 54, the shoulder 60 continues to advance the finger sleeve 70 and the finger 72. When the V-shaped bend 86 moves off the ramped portion 88 and onto a flat portion 98 of the trigger bracket 90 the trigger bracket 90 is moved outside of the stop 92 and the trigger 18 can be freely advanced in the direction of arrow 100.

Figure 6:
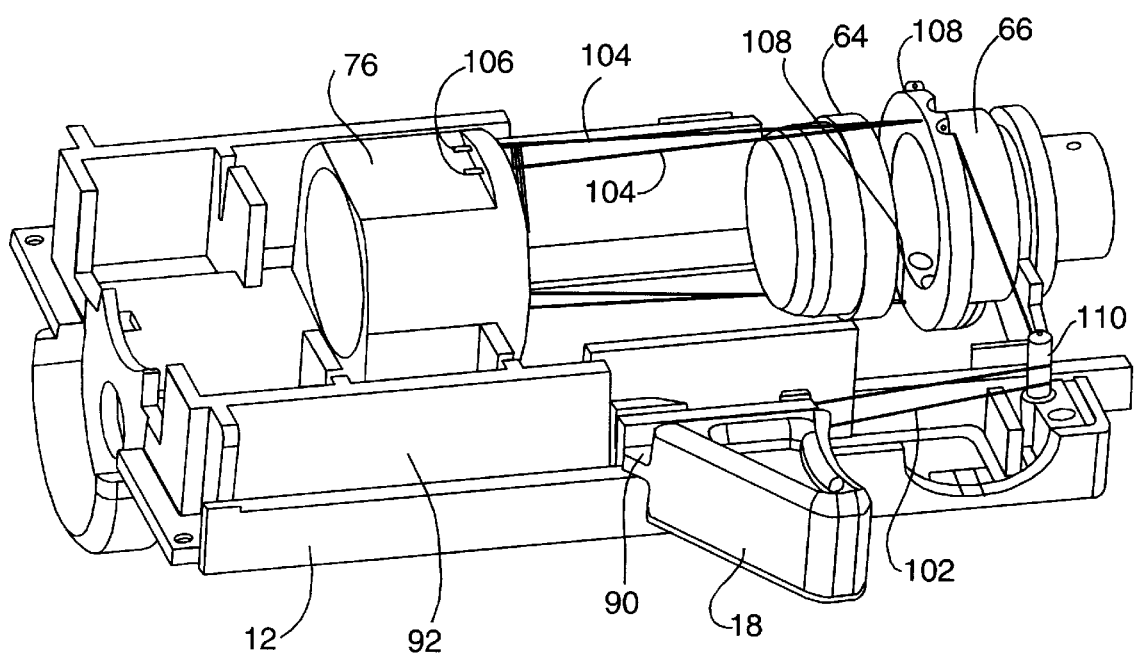
FIG. 6 is a perspective view of the trigger mechanism of a biopsy device designed according to the invention.

In FIG. 6, a partial side view of the trigger mechanism of the device is shown. Specifically, the routing pathway of a return cable 102 is shown. Each end of the return cable 102 is split into a pair of tails 104. One end of the return cable 102 is connected by a pair of stops 106 to an upper portion of the collar 76. The return cable 102 is routed through one of a pair of diametrically opposed holes 108 in the screw base 66 and around a cable post 10. The return cable 102 passes from the cable post 110 to the trigger bracket 90 and passes partially around a post (not shown) on the trigger bracket 90. The return cable 102 is then routed back around the cable post 110, through the other of the holes 108, and connects to a bottom portion of the collar 76.

Figure 7:
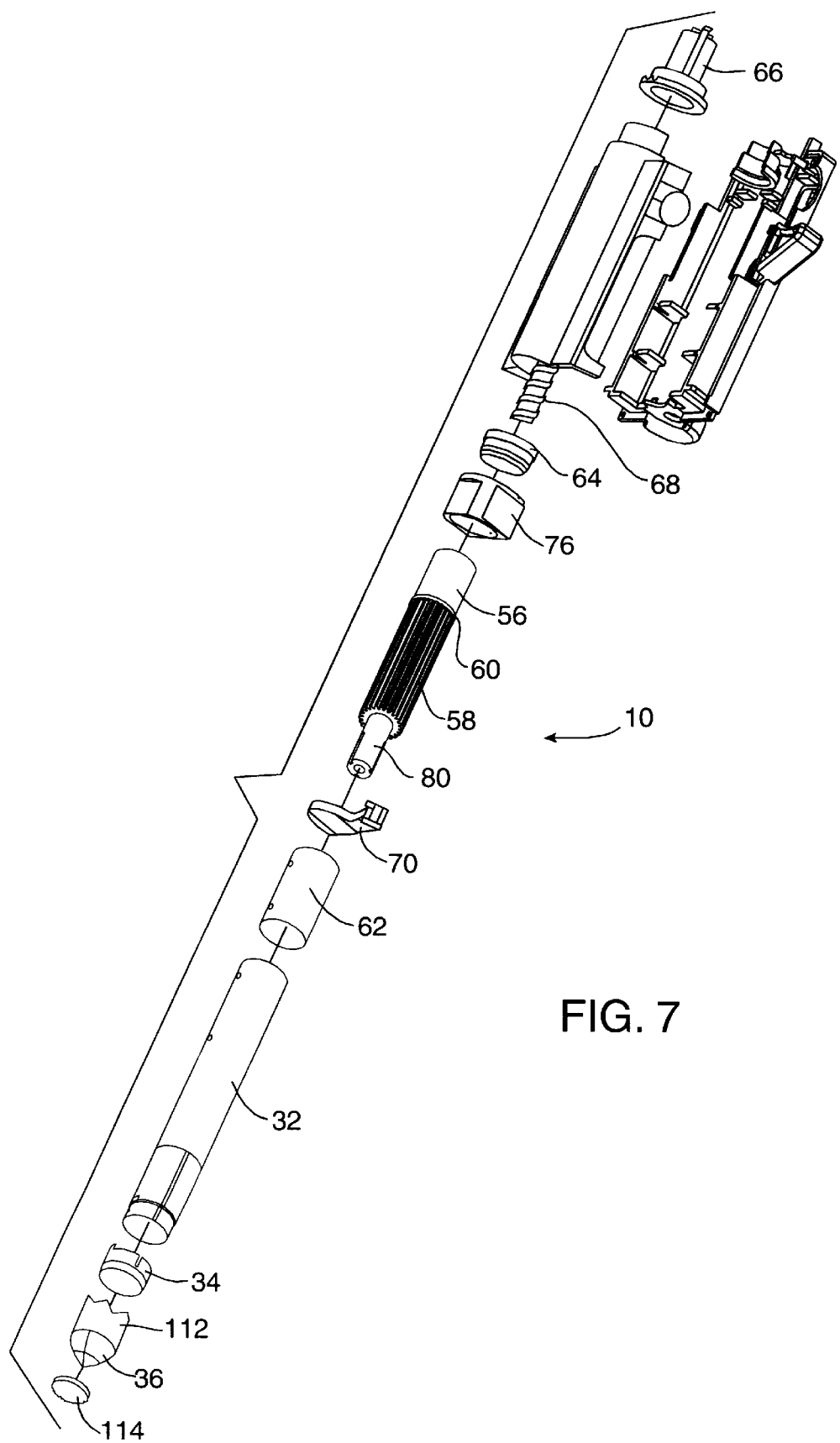
FIG. 7 is an exploded perspective view of a biopsy device according to the invention.

In FIG. 7, a partial exploded view of the biopsy device 10 is shown. The stylet 36 is mounted to one end of a retracting tube 112 that extends through the shaft 32 of the cannula 30, the central passage 82, and is fixedly mounted to the stylet retractor handle 20 (not shown). A circular cannula blade 114 is mounted over the stylet 36 onto a nose piece 34.

Figure 8:
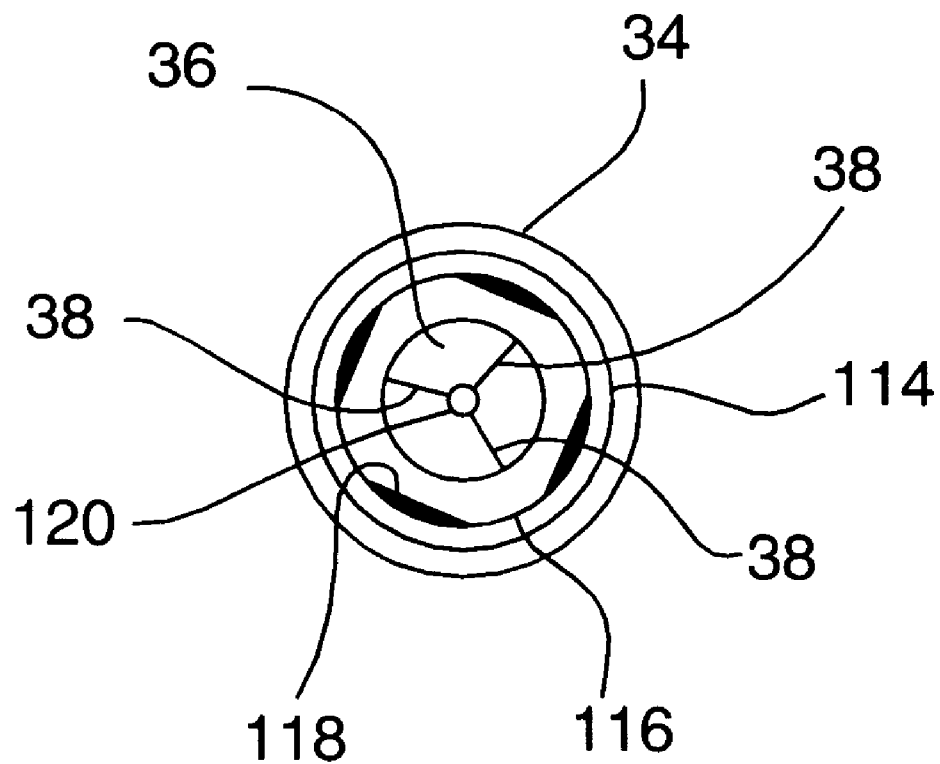
FIG. 8 is an end view of a cannula nose piece designed according to the invention.

FIG. 8 is an end view of the nose piece 34 and the stylet 36. The nose piece 34 surrounds the cannula blade 114. A garrote groove 116 is located within the nose piece 34 and accommodates a garrote (not shown). The garrote groove 116 includes a number of flat portions 118. A central passage 120 extends from the stylet 36 through the retracting tube 112 and the stylet retractor handle 20 to accommodate passage of the localization needle 22. The garrote (not shown) is mounted to the sleeve 64 and extends through the spline 54 and cannula 30 to the nose piece 34. As described above, the device 10 includes three separate cutting members including the blade 38 of the stylet 36, the circular cannula blade 114, and the garrote.

In the use of the device 10, the localization needle 22 exits the stylet tip 36 through the central passageway 120 and into the lesion. The safety wrapper 50 is then removed from the guide wire 26 and the guide wire 26 is pushed out the localization needle 22 and deploys in the region of the lesion. The device 10 is then manually advanced toward the lesion. ts the device is advanced the stylet 36 and the blades 38 work in conjunction to transect and separate tissue in route to the lesion. When the stylet 36 is adjacent the lesion manual advancement is stopped. The stylet 36 is retracted by the stylet retraction handle 20. Rotation of the adjustment knob 44 rotates the gear member 58. Rotation of the gear member 58 advances the spline 54 down the lead screw 68. Movement of the spline 54 advances the cannula blade 114 which cuts a core of tissue as the cannula blade 114 rotates and advances. Advancement of the cannula blade 114 can be monitored through the window 16. When the front of the gear member 68 becomes visible through the window 16 this indicates that the finger 72 has moved the trigger 18 to the fully unlocked position. At that position the trigger 18 can be pushed toward the cannula 30. This forward motion, through the action of the return cable 102 pulls the collar 76 toward the stylet retractor handle 20. As the collar 76 is pulled toward the stylet retractor handle 20 it engages the sleeve 64 and pulls it toward the stylet retractor handle 20. The retraction of the sleeve 64 causes closure of the garrote thus making a cut transverse to the direction of the advancement of the cannula blade 114 thereby producing a plug containing the lesion. Then the device 10 is removed from the breast.

We claim:

1. A device for removing suspect breast tissue comprising:
   a stylet mounted on a retracting handle, said stylet having a tip containing a plurality of blades for transecting tissue and a central passage capable of receiving a localization needle;
   a cannula mounted on a drive mechanism, said cannula having a shaft that supports a cutting surface opposite said drive mechanism;
   said drive mechanism for simultaneously rotating said cannula and moving said cannula in a direction that is transverse to the rotation of said cannula;
   a garrote for performing a cut transverse to the longitudinal axis of the cannula, said garrote mounted adjacent to said cutting surface of said cannula;
   a trigger for deploying said garrote, said trigger including a locking mechanism for preventing deployment of said garrote prior to movement of said cannula a predetermine distance, said locking mechanism has a locked position and an unlocked position, in the locked position the trigger abuts a trigger stop and in the unlocked position a ramp lifts the trigger above the trigger stop; and
   a localization needle having a guide wire mounted within said needle.

2. The device for removing suspect breast tissue of claim 1, wherein said guide wire is movable within the localization needle.

3. The device for removing suspect breast tissue of claim 2, wherein the locking mechanism prevents deployment of the garrote until a cutting plane of the garrote is beyond an end of the guide wire.

4. The device for removing suspect breast tissue of claim 2, wherein the guide wire includes a hook that anchors one end of the guide wire in the breast tissue.

5. The device for removing suspect breast tissue of claim 2, further comprising means for preventing premature deployment of the guide wire.

6. The device for removing suspect breast tissue of claim 1, wherein the ramp moves along a longitudinal axis of the device.

7. The device for removing suspect breast tissue of claim 1, wherein when the trigger is in the unlocked position, the trigger can be advanced to deploy the garrote and cut a plug of tissue.

8. The device for removing suspect breast tissue of claim 1, wherein the locking mechanism is moved from a locked position to an unlocked position by rotation of a gear member which causes longitudinal motion of a spline.

9. The device for removing suspect breast tissue of claim 8, wherein the rotation of the gear member also advances the cannula to cut a core of tissue.

10. A device for removing suspect breast tissue comprising:
    a stylet mounted on a retracting handle, said stylet having a tip containing a plurality of blades for transecting tissue and a central passage capable of receiving a localization needle;
    a cannula mounted on a drive mechanism, said cannula having a shaft that supports a cutting surface opposite said drive mechanism;
    said drive mechanism for simultaneously rotating said cannula and moving said cannula in a direction that is transverse to the rotation of said cannula;
    a garrote for performing a cut transverse to the longitudinal axis of the cannula, said garrote mounted adjacent to said cutting surface of said cannula; a trigger for deploying said garrote, said trigger including a locking mechanism for preventing deployment of said garrote prior to movement of said cannula a predetermine distance, said locking mechanism is moved from a locked position to an unlocked position by rotation of a gear member which causes longitudinal motion of a spline; and
    a localization needle having a guide wire mounted within said needle.

11. The device for removing suspect breast tissue of claim 10, wherein said guide wire is movable within the localization needle.

12. The device for removing suspect breast tissue of claim 11, wherein the locking mechanism prevents deployment of the garrote until a cutting plane of the garrote is beyond an end of the guide wire.

13. The device for removing suspect breast tissue of claim 11, wherein the guide wire includes a hook that anchors one end of the guide wire in the breast tissue.

14. The device for removing suspect breast tissue of claim 11, further comprising means for preventing premature deployment of the guide wire.

15. The device for removing suspect breast tissue of claim 10, wherein the locking mechanism has a locked position and an unlocked position, in the locked position the trigger abuts a trigger stop and in the unlocked position a ramp lifts the trigger above the trigger stop.

16. The device for removing suspect breast tissue of claim 15, wherein the ramp moves along a longitudinal axis of the device.

17. The device for removing suspect breast tissue of claim 15, wherein when the trigger is in the unlocked position, the trigger can be advanced to deploy the garrote and cut a plug of tissue.

18. The device for removing suspect breast tissue of claim 10, wherein the rotation of the gear member also advances the cannula to cut a core of tissue.

* * * * *